United States Patent [19]
Shisheva

[11] Patent Number: 6,110,718
[45] Date of Patent: Aug. 29, 2000

[54] MAMMALIAN PUTATIVE PHOSPHATIDYLINOSITOL-4-PHOSPHATE-5-KINASE

[75] Inventor: Assia Shisheva, Royal Oak, Mich.

[73] Assignee: Wayne State University, Detroit, Mich.

[21] Appl. No.: 09/045,201

[22] Filed: Mar. 20, 1998

[51] Int. Cl.[7] ............................. C12N 9/12; C12N 1/20; C12N 15/00; C12Q 1/68; C07H 21/04

[52] U.S. Cl. ................. 435/194; 435/320.1; 435/325; 435/252.3; 435/6; 536/23.2; 536/24.31

[58] Field of Search ............................. 435/194, 320.1, 435/252.3, 6, 325; 536/23.2, 24.31

[56] References Cited

U.S. PATENT DOCUMENTS

| | | | |
|---|---|---|---|
| 4,518,584 | 5/1985 | Mark et al. ........................ | 424/85 |
| 5,530,109 | 6/1996 | Goodearl et al. .................. | 536/23.5 |
| 5,708,157 | 1/1998 | Jacobs et al. ..................... | 536/23.5 |

OTHER PUBLICATIONS

Boronenkov, I.V. et al., "The Sequence of Phosphatidylinositol–4–phosphate 5–Kinase Defines a Novel Family of Lipid Kinases," *J. Biol. Chem.* 270:2881–2884 (1995).

Czech, M.P., "Molecular Action Of Insulin On Glucose Transport," *Annu. Rev. Nutr.* 15:441–471 (1995).

Hinchliffe, K. et al., "Inositol lipid pathways turn turtle," *Nature* 390:123–124 (1997).

Israel, D.I., "A PCR–based method for high stringency screening of DNA libraries," *Nucleic Acids Research* 21(11):2627–2631 (1993).

Liscovitch, M. et al., "Signal Transduction and Membrane Traffic: The PITP/Phosphoinostide Connection," *Cell* 81:659–662 (1995).

Loijens, J.C. et al., "The Phosphatidylinositol 4–Phosphate 5–Kinase Family," *Advanc. Enzyme Regul.* 36:115–140 (1996).

Rameh, L.E. et al., "A new pathway for synthesis of phosphatidylinositol–4,5–biphosphate," *Nature* 390:192–196 (1997).

Singh, H. et al., "Molecular Cloning of Sequence–Specific DNA Binding Proteins Using Recognition Site Probe," *Bio Techniques* 7(3):252–261 (1989).

Stenmark, H. et al., "Endosomal Localization of the Autoantigen EEA1 is Mediated by a Zinc–binding FYVE Finger," *The Journal Of Biological Chemistry* 271(39):24048–24054 (1996).

Toker, A. et al., "Activation of Protein Kinase C Family Members by the Novel Phosphophoinositides Ptdlns–3, 4–$P_2$ and Ptdlns–3,4,5–$P_3$," *The Journal Of Biological Chemistry* 269(51)32358–32367 (1994).

Yamamoto, A. et al., "Novel Pl(4)P 5–Kinase Homologue, Fab1p, Essential for Normal Vacuole Function and Morphology in Yeast," *Molecular Biology of the Cell* 6:525–539 (1995).

Zhang, X. et al., "Phosphatidylinositol–4–phosphate 5–Kinase Isozymes Catalyze the Synthesis of 3–Phosphate–containing Phosphatidylinositol Signaling Molecules," *The Journal Of Biological Chemistry* 272(28):17756–17761 (1997).

*Primary Examiner*—Rebecca E. Prouty
*Attorney, Agent, or Firm*—Lahive & Cockfield, LLP

[57] ABSTRACT

A novel mammalian phosphatidylinositol-4-phosphate-5-kinase (PIP5K) referred to herein as p235 and novel polynucleotides encoding p235, are provided. p235 is specifically expressed in adipocytes and myocytes and is believed to be involved in insulin-induced membrane trafficking. Therapeutic, diagnostic and research methods utilizing the novel polynucleotides and proteins are also provided.

14 Claims, 4 Drawing Sheets

FIG. 3A

```
p235    GKSGAAFYATEDDRFILK ·73aa- DLKGS ·59aa- IDYSLL ·9aa- LVGIID ·7aa- DKKLE
Fabip   GKSGSGSFFLKTLDDDRFIIK ·74aa- DLKGS ·56aa- MDYSLV ·9aa- LTVGIID ·7aa- DKKLE
CO5E.5  GKSGSGSFFYRTQDDRFVVK ·71aa- DLKGS ·57aa- MDYSLL ·9aa- LILGIVD ·7aa- DKKLE
PIP5KI  GASGSLFYVSSDDEFIIK ·54aa- DLKGS ·57aa- MDYSLL ·71aa- LYIGIID ·7aa- VKKLE
```

FIG. 3B

```
p235   PD·SQGKECYDCSEKFTITFRRRHHCRLCGQIFCSRCCNQEIPGKFMGYTGDLRACTYC  168-224
Fabip  KD·ESSKECFSCCGKTFNTFRRKHHCRICGQIFCSSCTLLIDGDRFGCHAKMFVCYNC  239-273
EEA1   ED·MEVQNCMACGKGFSVTVRRRHHCRQCGGNIFCAECSAKNALTPSS··KKPVRYCDA  1350-1384
Vps27  ADWIDSDACMICKKKFSLLNRKHHCRSCGQVFCQEHSSNSIPLPDLGIYEPVRVCDSC  175-225
Hrs-2  PDWVDAEECHRCRVQFGVVTRKHHCRACGQIFCGKCSSKYSTIPKFGIEKEVRVCEPC  163-215
             ·C  ·· C  C       HHC  C       C              C · · C
```

MAMMALIAN PUTATIVE PHOSPHATIDYLINOSITOL-4-PHOSPHATE-5-KINASE

FIELD OF THE INVENTION

The present invention relates generally to novel polynucleotides and the proteins encoded thereby and more particularly, to polynucleotides encoding a novel mammalian phosphatidylinositol-4-phosphate-5-kinase (PIP5K), and therapeutic, diagnostic and research methods employing same.

BACKGROUND OF THE INVENTION

Insulin action to recruit an intracellular pool of the glucose transporter protein GLUT4 to the fat/muscle cell surface has been established for more than a decade, yet the molecular details of this phenomenon are still elusive. Czech, M. P., *Ann. Rev. Nutr.* 15:441–471 (1995). Intriguingly, while GLUT4 appears to be a unique isoform for fat and muscle tissues, signaling element(s) specifically implicated in its sorting, directing and insulin-sensitive delivery to the cell surface are presently unknown. Phosphatidylinositol4-phosphate-5-kinase (PIP5K; EC2.7.1.68) has been implicated in membrane trafficking in yeast. Yamamoto, A. et al., *Mol. Biol. Cell.* 6:525–539 (1995). In particular, PIP5K synthesizes phosphatidylinositol 4,5-bisphosphate (Ptdlns[4,5]$P_2$) from phosphatidylinositol-4-phosphate (Ptdlns[4]P). Loijens, J. C. et al., *Advan. Enzyme Regul.* 36:115–140 (1996). It has recently been reported that PIP5K also synthesizes Ptdlns[4,5]$P_2$ from phosphatidylinositol-5-phosphate (Ptdlns[5]P). Hinchliffe, K. et al., *Nature* 390:123–124 (1997). The biosynthesis of Ptdlns[4,5]$P_2$ has attracted increasing interest because of mounting evidence implicating metabolites of Ptdlns[4,5]$P_2$ as important regulators of many cellular processes. Loijens, J. C. et al., *Advan. Enzyme Regul.* 36:115–140 (1996). In particular, Ptdlns[4,5]$P_2$ is a key substrate of insulin-activated PI 3-kinase, which enzyme, together with its Ptdlns[3,4]$P_2$ and Ptdlns[3,4,5]$P_3$ products, appear to be important elements in insulin action on GLUT4 membrane movements. Czech, M. P., *Ann. Rev. Nutr.* 15:441–471 (1995).

The key role of activated PI 3-kinase implies the presence of a large, easily available phosphoinositide substrate pool and suggests that the local production of Ptdlns[4]P and Ptdlns[4,5]$P_2$ lipid substrates at key insulin-sensitive intracellular locations would aid an efficient PI 3-kinase reaction and may be crucial for the PI 3- kinase-mediated effect of insulin in GLUT4 directing and delivery to the fat/muscle cell surface. In addition, an alternative pathway of generating Ptdlns[3,4]$P_2$ and Ptdlns[3,4,5]$P_3$ has been recently suggested which utilizes Ptdlns[3]P substrates and concert action of phosphatidylinositol-4-phosphate-5-kinases. Zhang, X. et al., *J. Biol. Chem.* 272:17756–17761 (1997). Taken together, these data are consistent with the notion that the activity of PIP5K can contribute to the regulated pools of Ptdlns[3,4]$P_2$ and Ptdlns[3,4,5]$P_3$ stimulated by growth factors and insulin.

Two distinct mammalian PlP5Ks, called type I (PIP5KI) and type II (PIP5KII), isolated from bovine and human erythrocytes, respectively, have been reported (Bazenet, C. E. et al., *J. Biol. Chem.* 265: 18012–18022 (1990); Jenkins, G. H. et al., *J. Biol. Chem.* 269:11547–11554 (1994)), as well as an isoform of PIP5KII (PIP5KIIa). Boronenkov, I. V. et al., *J. Biol. Chem.* 270:2881–2884 (1995). Yeast isozymes, specifically MSS4 and fab1, have also been isolated and studied. Yamamoto, A. et al., *Mol. Biol. Cell* 6:525–539 (1995); Yoshida, S. et al., *Mol. Gen. Genet.* 342:631–640 (1994); Yamamoto, A. et al., *Mol. Biol. Cell* 6:525–539 (1995).

As mentioned above, the conversion from Ptdlns[4]P to Ptdlns[4,5]$P_2$ is an important branchpoint in the phosphoinositide (PI) cycle, depicted in FIG. 1A. FIG. 1B depicts newly described inositol lipids, Ptdlns[5]P and Ptdlns[3,5]$P_2$, and FIG. 1C includes the novel alternative pathway for Ptdlns[3,4,5]$P_3$ production by PIP5Ks. The hydrolysis of Ptdlns[4,5]$P_2$ by phosphoinositide-specific phospholipase C(PLC; EC 3.1.4.3) generates the second messengers, 1,2-diacylglycerol and inositol 1,4,5-triphosphate. 1,2-diacylglycerol activates several protein kinase C isoforms while inositol 1,4,5-triphosphate causes an increase in intracellular calcium. Rana, R. S. *Physiol. Rev.* 70:115–164 (1990). Ptdlns[4,5]$P_2$ can also be phosphorylated by a PI 3-kinase (EC 2.7.1.137) to phosphatidylinositol 3,4,5-triphosphate (Ptdlns[3,4,5]$P_3$), a second messenger whose targets are largely unknown but may include protein kinase C isoforms. Nakanishi, H. et al., *J. Biol. Chem.* 268:13–16 (1993); Toker, A. et al., *J. Biol. Chem.* 269:32358–32367 (1994). Furthermore, Ptdlns[4,5]$P_2$ modulates the function of numerous enzymes including many actin-binding proteins (Janmey, P. A., *Annu. Rev. Physiol.* 56:169–191 (1994)), binds Ph domains found in some signaling proteins (Harlan, J. E. et al., *Nature* 371:168–170 (1994)), and appears to be involved in the secretory vesicle cycle. Eberhard, D. A. et al., *Biochem. J.* 268:15–25 (1990); Hay, J. C. et al., *Nature* 374:173–177 (1995); Liscovitch M. et al., *Cell* 81:659–662 (1995).

PIP5Ks have been isolated from erythrocytes, brain, adrenal medulla, liver and other sources. Carpenter, C. L. et al., *Biochemistry* 29:11147–11156 (1990) (and references therein); Van Dongen, C. J. et al., *Biochem. J.* 233:859–864 (1986); Moritz, A et al., *Biochim. Biophys. Acta* 1168:79–86 (1993); Divecha, N. et al., *Biochem. J.* 288:637–642 (1992); Husebye, E. S. et al., *Biochim. Biophys. Acta* 1010:250–257 (1989); Urumow, T. et al., *Biochim. Biophys. Acta* 1052:152–158 (1990). In cells, PIP5K activity is found on the plasma membrane (Carpenter, C. L. et al., *Biochemistry* 29:11147–11156 (1990); Urumow, T. et al., *Biochim. Biophys. Acta* 1052:152–158 (1990); Ling, L. E. et al., *J. Biol. Chem.* 264:5080–5088 (1989); Smith, C. D. et al., *J. Biol. Chem.* 264:3206–3210 (1989); Bazenet, C. E. et al., *J. Biol. Chem.* 265:18012–18022 (1990); Jenkins, G. H. et al., J. Biol. Chem. 269:11547-11554 (1994)), associated with the cytoskeleton (Payrastre, B. et al., *J. Cell Biol.* 115:121–128 (1991); Grondin, P. et al., *J. Biol. Chem.* 266:15705–15709 (1991)), on the endoplasmic reticulum (Helms, J. B. et al., *J. Biol. Chem.* 266:21368–21374 (1991), and in nuclei (Divecha, N. et al., *Biochem. J.* 289:617–620 (1993); Payrastre, B. et al., *J. Biol. Chem.* 267:5078–5084 (1992); Divecha, N. et al., *Cell* 74:405–407 (1993)). There is also a soluble, cytosolic population of PIP5K. Ling, L. E. et al., *J. Biol. Chem.* 264:5080–5088 (1989); Bazenet, C. E. et al., *J. Biol. Chem.* 265:18012–18022 (1990); Jenkins, G. H. et al., *J. Biol. Chem.* 269:11547–11554 (1994); Moritz, A. et al., *J. Neurochem.* 54:351–354 (1990). The kinase's product, Ptdlns[4,5]$P_2$, is primarily found in the plasma membrane but can be detected in isolated endoplasmic reticulum and nuclei. Helms, J. B. et al., *J. Biol. Chem.* 266:21368–21374 (1991); Tran, D. et al., *Cell. Signal* 5:565–581 (1993). Ptdlns[4]P is present in all of these fractions.

Helms, J. B. et al., *J. Biol. Chem.* 266:21368–21374 (1991); Tran, D. et al., *Cell. Signal* 5:565–581 (1993). Hinchliffe, K. et al., *Nature* 390:123–124 (1997); Rameh, L. E. et al., *Nature* 390:192–196 (1997).

One postulated reason for the large family of PIP5Ks is that many forms of regulation and cellular functions have been attributed to PIP5Ks, as summarized in FIG. 2. It would thus be desirable to provide a mechanism to further study the role of PIP5Ks. It would also be desirable to provide a novel mammalian PIP5K. It would further be desirable to provide a screening method for further studying the role of PIP5Ks, their substrates and products. It would still further be desirable to provide an animal model for further investigating the role of PlP5Ks.

SUMMARY OF THE INVENTION

A novel polynucleotide encoding a mammalian PIP5K referred to herein as p235, is provided. p235 is specifically expressed in adipocytes and myocytes and is believed to be involved in membrane trafficking, particularly, insulin-induced membrane trafficking of fat/muscle specific glucose transporter, GLUT4. The isolated cDNA for p235 set forth in SEQ ID NO: 1 is about 7.4 kbp long with an open reading frame extending from nucleotide 139 to 6294, encoding the novel protein. p235 is 2052 amino acids in length with Mr 233,040 and pI 6.34. The deduced polypeptide sequence is set forth in SEQ ID NO: 2.

Thus, in one embodiment, the present invention provides a composition comprising an isolated polynucleotide selected from the group consisting of:
 a) a polynucleotide comprising the nucleotide sequence of SEQ ID NO: 1,
 b) a polynucleotide encoding a protein comprising the amino acid sequence of SEQ ID NO: 2,
 c) a polynucleotide encoding a protein comprising a fragment of the amino acid sequence of SEQ ID NO: 2, having biological activity,
 d) a polynucleotide which is an allelic variant of the polynucleotide of a) and,
 e) a polynucleotide which encodes a species homologue of the protein of b) or c).

In another embodiment, the present invention provides a gene corresponding to the cDNA of SEQ ID NO: 1.

In yet another embodiment, the present invention provides a composition comprising a protein wherein the protein comprises an amino acid sequence selected from the group consisting of:
 a) the amino acid sequence of SEQ ID NO: 2, and
 b) fragments of the amino acid sequence of SEQ ID NO: 2.

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing a protein, which comprise:
 (a) growing a culture of the host cell transformed with such polynucleotide compositions in a suitable culture medium; and
 (b) purifying the protein from the culture.

The protein produced according to such methods is also provided by the present invention. Preferred embodiments include those in which the protein produced by such process is a mature form of the protein.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

Methods of using the polynucleotide of the present invention and the protein encoded thereby to further study the role of PIP5Ks, their substrates and products, are also provided as well as research models including cell lines and transgenic and knockout animal models.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 3A shows the similarity between a subset of highly conserved motifs in the PIP5K domain of mouse p235, yeast Fab1 p, C. elegans C05E7.5 and human PIP5K Type I [Accession numbers: pirll556274 (Fab1p); pirllA57013 (EEA1); pirllS45129 (Vsp27); gill885385 (Hrs-2); gil065686 (C05E7.5) and, gi1743875 (PI(4) 5-kinase)]; and FIG. 3B shows the similarity between the FYVE motif in a conserved zinc-binding region. Potential $Zn^{2+}$-coordinating his/cis clusters are indicated below the alignment.

DETAILED DESCRIPTION OF THE PREFERRED EMBODIMENTS

Figure 1A:
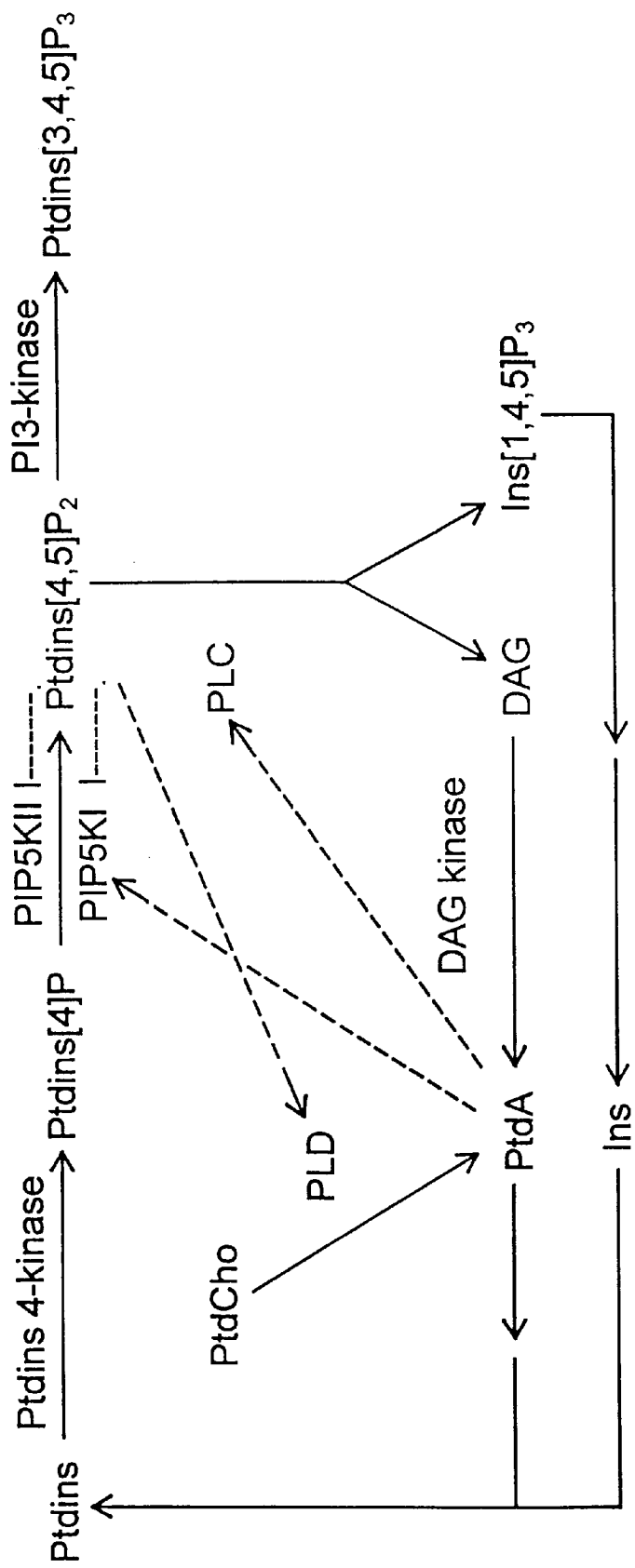
FIGS. 1A–1C are schematics of the phosphoinositide cycle.
Figure 1B:
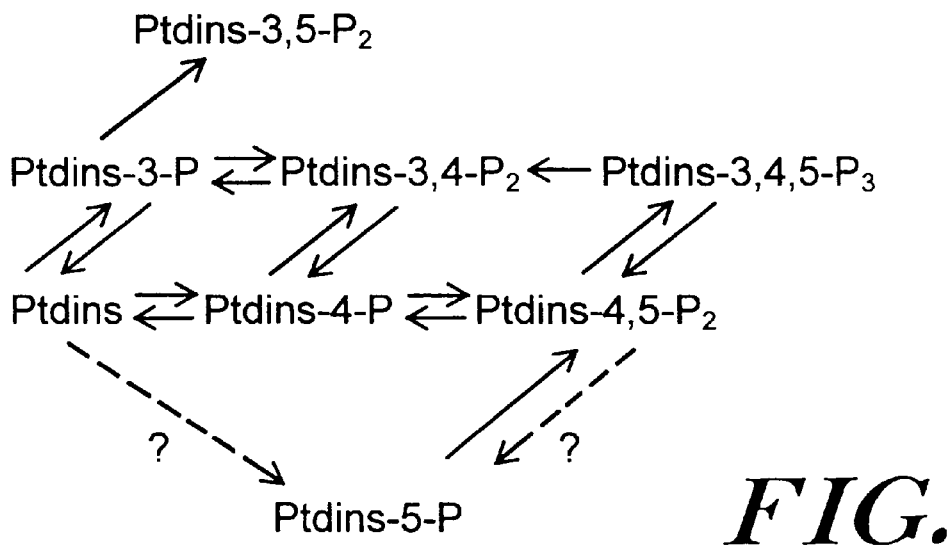
Figure 1C:
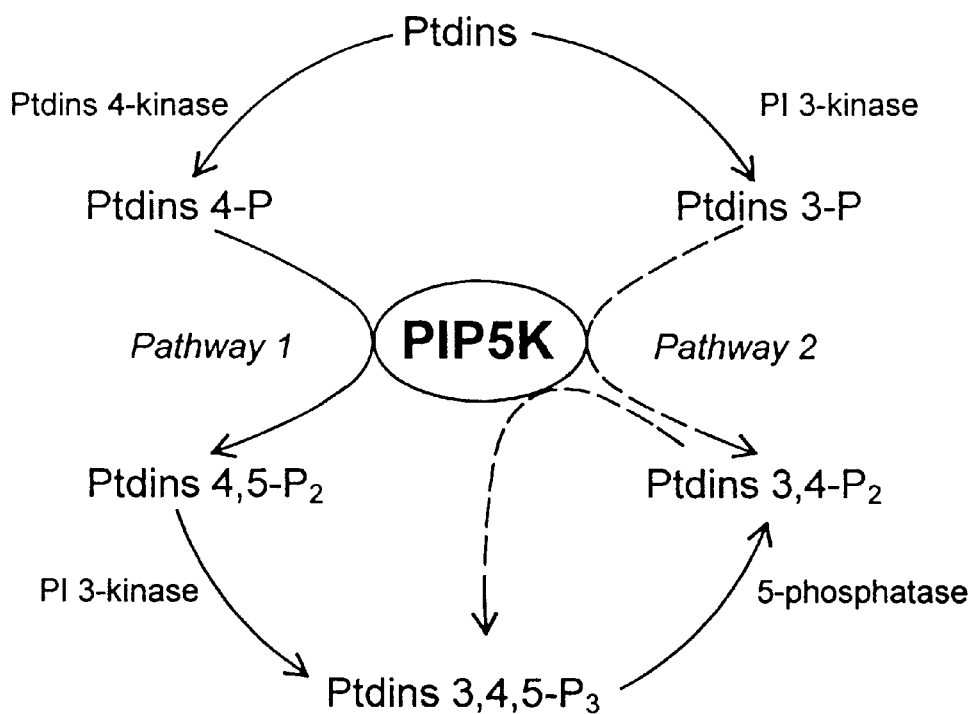
Figure 2:
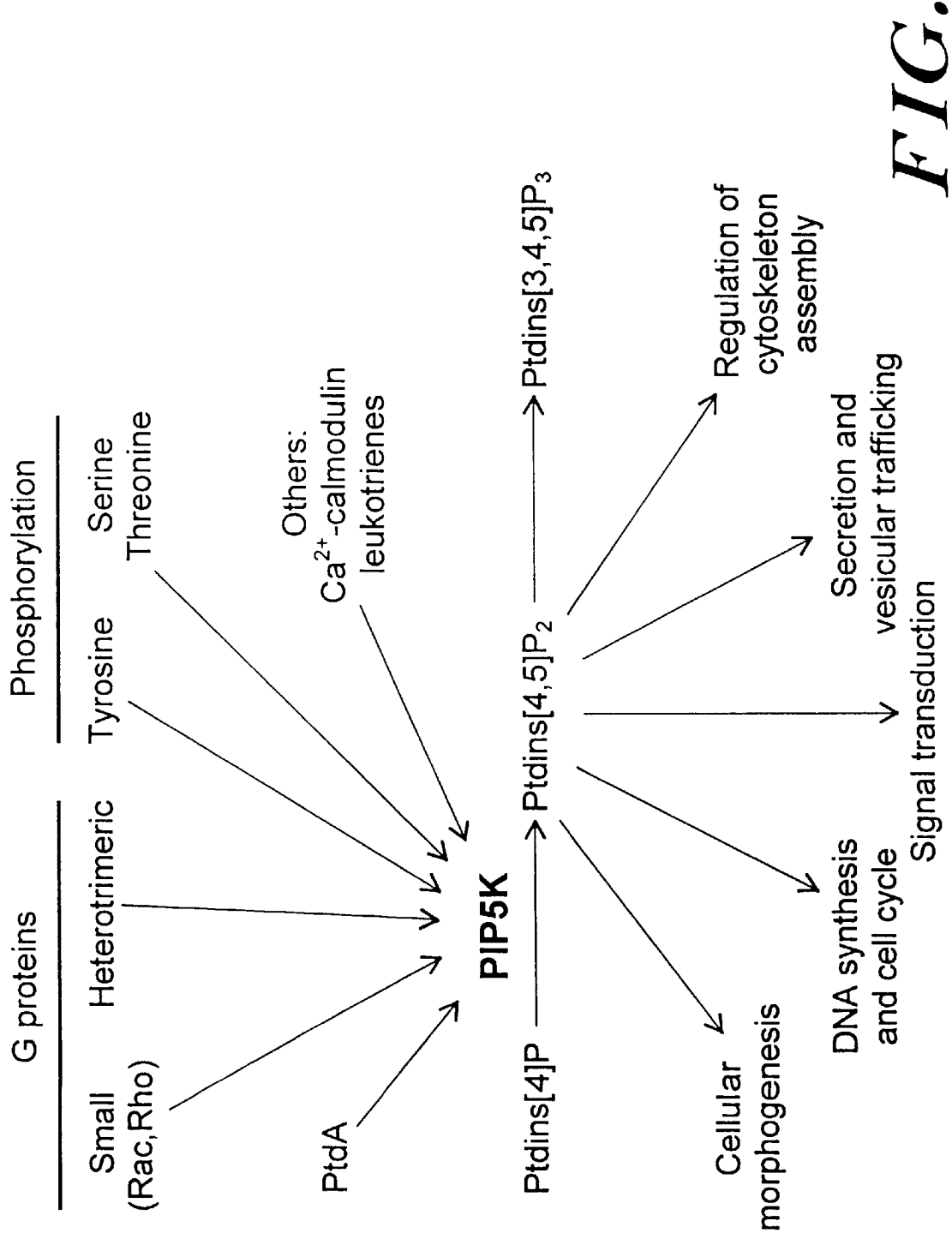
FIG. 2 is a schematic of the regulation of the PIP5K isoforms and the cellular roles of PtdIns[4,5]$P_2$ synthesized by these enzymes.

A novel mammalian PIP5K referred to herein as p235, is provided. The isolated cDNA is about 7.4 kbp long with an open reading frame extending from nucleotide 139 to 6294, encoding the novel mammalian protein, p235. p235 is 2052 amino acids in length with estimated Mr 233,040 and pI 6.34. The predicted ATG initiation codon conforms well to the Kozak consensus sequence for the translation initiation start and is preceded by an in-frame terminator (nucleotide 78), supporting the notion that this ATG represents the translation initiator of the p235 gene product.

Without intending to be bound by theory, it is believed that p235 may be involved in membrane trafficking, and in particular, GLUT4 translocation induced by insulin, that results in glucose transport into cells. Thus, by employing p235 and the polynucleotides encoding same, movement of GLUT4 onto the cell surface, e.g., adipocyte and myocyte surfaces, may be promoted. Likewise, by inhibiting p235 function, GLUT4 movement onto the cell surface may be inhibited.

Increasing glucose uptake in cells by employing p235 and the polynucleotides encoding same may provide effective treatment of diseases involving a deficiency in glucose transport. For example, non-insulin-dependent diabetes mellitus (NIDDM) also known as Type 2 diabetes, is characterized by a decrease in the body's ability to utilize insulin. This resistance to insulin action is thought to be caused by either a significant reduction in the number of insulin receptors, a defect in the receptors preventing insulin binding, or a defect in the downstream signalling after insulin has bound to the receptor. Any of these defects result in a significant decrease in the amount of glucose taken up by the cells and an increase in the concentration of blood glucose. Increased cellular uptake of glucose by patients diagnosed with NIDDM may be obtained by providing increased levels of p235 to those cells.

Inhibition of p235 function and sequence inhibition of glucose transporter movement into cells, particularly adipocytes, may provide a treatment for obesity. Glucose is the main source of energy for adipocytes as metabolism of glucose provides the building blocks for synthesis of triacylglycerols, the main components of adipocytes. Blocking the uptake of glucose would decrease the amount of adipose tissue. Inhibiting p235 function is therefore one method for blocking the uptake of glucose and decreasing the amount of adipose tissue.

The nucleic acid sequence of the cDNA encoding p235 and its deduced amino acid sequence are set forth in SEQ ID NOS: 1 and 2, respectively. In a preferred embodiment, the isolated nucleic acid molecule of the invention comprises the nucleotide sequence of SEQ ID NO: 1, or homologues therefore. In another preferred embodiment, the isolated and purified polypeptide of the invention comprises the amino acid sequence of SEQ ID NO: 2, as well as biological equivalents.

Database analysis of the deduced amino acid sequence reveals that p235 contains, in order from its N-terminus, a zinc-binding motif, a large chaperonin-like region, and spread over the C-terminal portion, a putative catalytic domain of PIP5K. The overall architecture and size of p235 are thus very similar to the yeast Fab1p. Yamamoto, A. et al., *Mol. Biol. Cell.* 6:525–539 (1995). The putative catalytic region of p235 displays a high sequence similarity to those of human PIP5K Type I, Fab1p and *C. elegans* C05E7.5, and includes a predicted downstream nucleotide binding motif and sequences (FIG. 3A). This similarity suggests that p235 has a PIP5K activity. Intriguingly, p235 shares no homology with the mammalian PIP5K outside the kinase domain and is distinguished in having additional sequences on the N-terminal side of the catalytic domain. Thus, the very N-terminus of p235 shows a striking similarity to a domain denoted as FYVE finger, recently identified in eleven non-nuclear proteins such as EEA1, Fab1p, Vsp27, and Vac1, implicated in membrane trafficking. Stenmark, H. et al., *J. Biol. Chem.* 271:24048–24054 (1996). The FYVE finger has been defined as a genuine zinc-binding domain that determines specific endosomal localization and is characterized by 8 conserved cysteines and 2 histidines as potential coordinators of zinc (FIG. 3B). Taken together, these results are consistent with the idea that the characteristic FYVE finger localizes p235 to endosomes where it acts to increase the local production of PtdIns[4,5]$P_2$ and/or PtdIns[3,4,5]$P_3$, important elements in insulin signaling of GLUT4 translocation.

To confirm p235 fat/muscle specific or enriched expression, Northern blot analysis (total RNA) of several cell types was performed. This analysis revealed that p235 mRNA is a single ~9 kb transcript, highly abundant in insulin-serisitive L6 monocytes and 3T3-L1 adipocytes, while in COS, CHO, HeLa and MCF-7 cells the message is undetectable. Intriguingly, although highly enriched in insulin-sensitive adipocytes and myocytes, the p235 transcript exists in the fibroblastic lines. These data indicate that the transcript level of p235 increases in fully differentiated insulin-responsive cells.

Fragments of the protein of the present invention which are capable of exhibiting biological activity are also encompassed by the present invention. Fragments of the protein may be in linear form or they may be cyclized using known methods, for example, as described in H. U. Saragovi, et al., *BioTechnology* 10:773–778 (1992) and in R. S. McDowell et al., *J. Amer. Chem. Soc.* 114:9245–9253 (1992). Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides a gene corresponding to the cDNA sequence disclosed herein. The corresponding gene can be isolated in accordance with known methods using the sequence information disclosed herein. Such methods include the preparation of probes or primers from the disclosed sequence information for identification and/or amplification of genes in appropriate genomic libraries or other sources of genomic materials.

In another aspect, DNA sequence information provided by the present invention allows for the preparation of relatively short DNA (or RNA) sequences or probes that are identical to or hybridize to the nucleotide sequence disclosed herein. Nucleic acid probes (also referred to as oligonucleotide probes) of an appropriate length are prepared based on a consideration of the nucleotide sequence of SEQ ID NO: 1. The probes can be used in a variety of assays appreciated by those skilled in the art, for detecting the presence of complementary sequences in a given sample. The probes may be useful in research, prognostic and diagnostic applications. For example, the probes may be used to detect homologus nucleotide sequences, e.g., the human homolog. The design of the probe should preferably follow these parameters:

a) it should be designed to an area of the sequence which has the fewest ambiguous bases ("N's"), if any; and b) it should be designed to have a $T_m$ of approximately 80° C. (assuming 2 degrees for each A or T and 4 degrees for each G or C). The oligonucleotide should preferably be labeled with y-$^{32}$P ATP (specific activity 6000 Ci/mole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/mole.

A further preferred nucleic acid sequence employed for hybridization studies or assays includes probe molecules that are complementary to at least a 10 to 70 or so long nucleotide stretch of the polynucleotide sequence shown in SEQ ID NO: 1. A size of at least 10 nucleotides in length helps to ensure that the fragment will be of sufficient length to form a duplex molecule that is both stable and selective. Molecules having complementary sequences over stretches greater than 10 bases in length are generally preferred in order to increase stability and selectivity of the hybrid, and thereby improve the quality and degree of specific hybrid molecules obtained. It will be appreciated that nucleic acid molecules having gene-complementary stretches of 25 to 40 nucleotides, 55 to 70 nucleotides, or even longer where desired, may be preferred. Such fragments can be readily prepared by, for example, directly synthesizing the fragment by chemical means, by application of nucleic acid reproduction technology, such as the PCR technology of U.S. Pat. No. 4,603,102, or by excising selected DNA fragments from recombinant plasmids containing appropriate inserts and suitable restriction enzyme sites. In certain embodiments, it is also advantageous to use oligonucleotide primers. The sequence of such primers is designed using the polynucleotide of the present invention and is used with PCR technology.

The invention also encompasses allelic variants of the disclosed polynucleotide or protein; that is, naturally-occurring alternative forms of the isolated polynucleotide which also encode proteins which are identical, homologous or related to that encoded by the polynucleotide.

The isolated polynucleotide of the invention may be operably linked to an expression control sequence such as the pMT2 or pED expression vectors disclosed in Kaufman et al., *Nucleic Acids Res.* 19:4485–4490 (1991), in order to produce the protein recombinantly. Many suitable expression control sequences are known in the art. General methods of expressing recombinant proteins are also known and are exemplified in R. Kaufman, *Methods in Enzymology* 185:537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide\expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coil, Bacillus subtills, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit) and such methods are well known in the art, as described in Summers and Smith, *Texas Agricultural Experiment Station Bulletin No. 1555* (1987). As used herein, an insect cell capable of expressing a polynucleotide of the present invention is "transformed."

The protein of the invention may be prepared by culturing transformed host cells under culture conditions suitable to express the recombinant protein. The resulting expressed protein may be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST), hexahistidine or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the protein of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified protein in screening of therapeutic compounds and in immunological processes for the development of antibodies.

The protein provided herein also include protein characterized by amino acid sequences similar to those of purified protein but into which modifications are naturally provided or deliberately engineered. For example, modifications in the peptide of DNA sequences can be made by those skilled in the art using known techniques. Modifications of interest in the protein sequence may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584).

Preferably, such alteration, substitution, replacement, insertion or deletion retains the desired activity of the protein.

Other fragments and derivatives of the sequence of the protein which would be expected to retain protein activity in whole or in part may thus be useful for screening or other immunological methodologies may also be easily made by those skilled in the art given the disclosures herein. Such modifications are believed to be encompassed by the present invention.

In one embodiment, the present invention provides an antibody immunoreactive with the p235 polypeptide. Also contemplated by the present invention are antibodies immunoreactive with homologues or biologically equivalent polynucleotides and polypeptides of the present invention. As used herein, the term "antibody" is used in its broadest sense to include polyclonal and monoclonal antibodies, as well as polypeptide fragments of antibodies that retain a specific binding activity for p235. One skilled in the art will appreciate that anti-p235 antibody fragments such as Fab, F(ab')$_2$ and Fv fragments can retain specific binding activity for p235 and, thus, are included within the definition of an antibody. In addition, the term "antibody" as used herein includes naturally occurring antibodies as well as non-naturally occurring antibodies and fragments that retain binding activity. Methods of making antibodies are known in the art. See, e.g., Harlow and Lane, *Antibodies: A Laboratory Manual* (Cold Spring Harbor Press, 1988).

As used herein, the term "nucleic acid" is intended to mean natural and synthetic linear and sequential arrays of nucleotides and nucleosides, e.g. in cDNA, genomic DNA (gDNA), mRNA, and RNA, oligonucleotides, oligonucleosides and derivatives thereof. It will also be appreciated that such nucleic acids can be incorporated into other nucleic acid chains referred to as "vectors" by recombinant-DNA techniques such as cleavage and ligation procedures. The terms "fragment" and "segment" are as used herein with reference to nucleic acids (e.g., cDNA, genomic DNA, i.e., gDNA) are used interchangeably to mean a portion of the subject nucleic acid such as constructed artificially (e.g. through chemical synthesis) or by cleaving a natural product into a multiplicity of pieces (e.g. with a nuclease or endonuclease to obtain restriction fragments). As used herein, "A" represents adenine; "T" represents thymine; "G" represents guanine; "C" represents cytosine; and "U" represents uracil.

As referred to herein, the term "encoding" is intended to mean that the subject nucleic acid may be transcribed and translated into the subject protein in a cell, e.g. when the subject nucleic acid is linked to appropriate control sequences such as promoter and enhancer elements in a suitable vector (e.g. an expression vector) and the vector is introduced into a cell. The term "polypeptide" is used to mean three or more amino acids linked in a serial array.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID NO: 1 or portion thereof), with a second target nucleic acid sequence. "High stringency conditions" for the annealing process may involve, for example, high temperature and/or low salt content, which disfavor hydrogen bonding contacts among mismatched base pairs. "Low stringency conditions" would involve lower temperature, and/or lower salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6× SSC at about 45° C., followed by a wash of 2X SSC at 50° C. are known to those skilled in the art or can be found in *Current Protocols in Molecular Biology*, John Wiley & Sons, N.Y. (1989), 6.31–6.3.6. For example, the salt concentration in the wash step can be selected from a low stringency of about 2× SSC at 50° C. to a high stringency of about 0.2× SSC at 50° C. In addition, the temperature in the wash step can be increased from low stringency at room temperature, about 22° C., to high stringency conditions, at about 75° C. Other stringency parameters are described in Maniatis, T., et al., *Molecular Cloning: A Laboratory Manual,* Cold Spring Harbor Laboratory Press, Cold Spring N.Y., (1982), at pp. 387–389; see also Sambrook J. et al., *Molecular Cloning: A Laboratory Manual,* Second Edition, Volume 2, Cold Spring Harbor Laboratory Press, Cold Spring, N.Y. at pp. 8.46–8.47 (1989).

As used herein, the term "specifically binds" refers to a non-random binding reaction between two molecules, for example between an antibody molecule immunoreacting with an antigen.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of 1) DNA from some portion of the gene (exon sequence, intron sequence, and/or promoter sequence) to be suppressed and 2) a marker sequence used to detect the presence of the knockout construct in the cell. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

The term "marker sequence" refers to a nucleic acid sequence that is 1) used as part of a nucleic acid construct (i.e., the "knockout construct") to disrupt the expression of the gene(s) of interest (e.g., p235), and 2) used as a means to identify those cells that have incorporated the knockout construct into the genome. The marker sequence may be any sequence that serves these purposes, although typically it will be a sequence encoding a protein that confers a detectable trait on the cell, such as an antibiotic resistance gene or an assayable enzyme not typically found in the cell. Where the marker sequence encodes a protein, the marker sequence will also typically contain a promoter that regulates its expression.

The term "progeny" refers to any and all future generations derived and descending from a particular mammal, i.e., a mammal containing a knockout construct inserted into its genomic DNA. Thus, progeny of any successive generation are included herein such that the progeny, the F1, F2, F3, generations and so on indefinitely are included in this definition.

The foregoing and other aspects of the invention may be better understood in connection with the following examples, which are presented for purposes of illustration and not by way of limitation.

SPECIFIC EXAMPLE 1

Isolation, Identification and Characterization of P235

To isolate the full length cDNA of the novel mammalian PIP5K, a mouse F442A adipocyte cDNA library was screened, first, with the isolated oligonucleotide probe and, subsequently, with probes derived from the positive clones, in close proximity to 5'- or 3'-ends. The isolated cDNA is about 7.4 kpb long with an open reading frame extending from nucleotide 139 to 6294 that encodes a novel mammalian protein of 2052 amino acids with estimated Mr 233,040 (p235). The predicted ATG initiation codon conforms well to the Kozak consensus sequence for the translation initiation start and is preceded by an in-frame terminator (nucleotide 78), thus supporting the notion that this ATG represents the translation initiator of the p235 gene product.

Database analysis of the deduced amino acid sequence reveals that p235 contains, in order from its N-terminus, a zinc-binding motif, a large chaperonin-like region, and spread over the C-terminal portion, a putative catalytic domain of PIP5K. The overall architecture and size of p235 are thus very similar to the yeast Fab1p. Yamamoto, A. et al., *Mol. Biol. Cell.* 6:525–539 (1995). The putative catalytic region of p235 displays a high sequence similarity to those of human PIP5K Type I, Fab1p and *C. eleganse* C05E7.5, and includes a predicted downstream nucleotide binding motif and sequences (FIG. 3A). This similarity suggests that p235 has PIP5K activity. Intriguingly, p235 shares no homology with the mammalian PIP5K outside the kinase domain and is distinguished in having additional sequences on the N-terminal side of the catalytic domain. Thus, the very N-terminus of p235 shows a striking similarity to a domain denoted as FYVE finger, recently identified in eleven non-nuclear proteins such as EEA1, Fab1p, Vsp27, and Vac1, implicated in membrane trafficking. Stenmark, H. et al., *J. Biol. Chem.* 271:24048–24054 (1996). The FYVE finger has been defined as a genuine zinc-binding domain that determines specific endosomal localization and is characterized by 8 conserved cysteines and 2 histidines as potential coordinators of zinc (FIG. 3B). Taken together, these results are consistent with the idea that besides PIP5K activity, p235 has additional biological functions related to membrane trafficking, perhaps by acting as yet to be identified, endosomal molecular elements through its zing-binding finger.

To confirm p235 fat/muscle specific or enriched expression, Northern blot analysis (total RNA) of several cell types was performed. This analysis revealed that p235 mRNA is a single ~9 kb transcript, highly abundant in insulin-sensitive L6 monocytes and 3T3-L1 adipocytes, while in COS, CHO, HeLa and MCF-7 cells the message is undetectable. Intriguingly, although highly enriched in insulin-sensitive adipocytes and myocytes, the p235 transcript exists in the fibroblastic lines. These data indicate that the transcript level of p235 increases in fully differentiated insulin-responsive cells.

To further define the specific function of p235 related to insulin-regulated GLUT4 membrane dynamics requires further studies on its cellular location, precise enzyme activity, and characterization of the specific targets of its product, PtdIns[4,5]$P_2$. The identification of p235 in insulin-sensitive cells and isolation of its cDNA provide methods for studying this phenomena.

SPECIFIC EXAMPLE 2

Research Uses and Utilities

The polynucleotide(s) provided by the present invention can be used by the research community for various purposes. The polynucleotide can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic finger-printing; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., *Cell* 75:791–803 (1993)) to identify polynucleotides encoding the other protein with which binding occurs or to identify inhibitors of the binding interaction.

The protein provided by the present invention can similarly be used in assays to determine biological activity, including a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

The gene encoding p235 (SEQ ID NO:1), or oligonucleotide fragments of said gene, can be used as bait in a yeast two hybrid system to detect proteins that interact specifically with p235. For example, the p235 gene can be expressed as a fusion protein with the DNA-binding site of the GAL4 transcription factor, and a second gene co-expressed as a fusion with the transcriptional activator domain of GAL4. The second gene can be a gene for a known protein or from a cDNA library. If the protein expression by the second gene interacts directly with p235, the two GAL4 domains are held in close enough proximity to trigger expression of a receptor such as lac-Z. Fritz, C. C. et al., *Current Biol.* 2:403–405 (1992). Expression of the reporter gene is usually determined using fluorescent or colormetric substrates. It will be appreciated by those skilled in the art that other two domain report proteins besides GAL4 can be used.

Likewise, the gene of SEQ ID NO:1 or oligonucleotides derived from said gene, can be used as a probe to screen DNA libraries. Such techniques include Northern hybridization blotting and PCR-based screening. Israel, D. I., *Nuc. Acids. Res.* 21:2627–2631 (1993).

Protein probes can also be used for screening DNA libraries. Antibodies to a specific protein such as p235 (SEQ ID NO:2) will bind to the desired protein, indicating that the DNA of interest is present. "Current Protocols in Molecular Biology," Section 6.7, John Wiley & Sons, Ausubel, F. et al. eds., 1995. The antibody itself may contain either a radioactive enzyme such as alkaline phosphatase. Alternatively, binding of the antibody may be determined using a labeled secondary antibody. Protein-protein interactions can also be utilized in screening DNA libraries by labeling the protein of interest, i.e. p235 with a radioactive tag and monitoring protein-protein interactions observed. Margolis, B. et al., *Meth. Enzymol.* 255:360–369 (1995).

It will be appreciated by those skilled in the art that any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual," 2d ed. Cold Spring Harbor Laboratory Press, Sambrook J., E. F. Fritsch and T. Maniatis eds., 1989, and "Methods in Enzymology: Guide to Molecular Cloning Techniques," Academic Press, Berger, S. L. and A. R. Kimmel eds., 1987.

In one preferred embodiment of the invention, a method of detecting the presence of p235 in a sample is provided, wherein the method comprises the steps of administering to the sample a nucleic acid probe specific for p235 and detecting hybridization of the probe and nucleotide sequences encoding p235 in the sample. The methods used to detect the presence of p235 may include, without limitation, amplification of the nucleic acid sequences encoding for p235 by PCR or other methods known to those skilled in the art. Hybridization may be carried out under stringent conditions. The sample may be any suitable biological sample including, but not limited to, tissue, blood, semen and urine.

In yet another preferred embodiment, the present invention contemplates a process of detecting a messenger RNA transcript that encodes the polypeptide of the present invention, wherein the process comprises (a) hybridizing the messenger RNA transcript with a polynucleotide sequence that encodes that polypeptide to form a duplex; and (b) detecting the duplex. Alternatively, the present invention provides a process of detecting a DNA molecule that encodes the polypeptide of the present invention, wherein the process comprises (a) hybridizing DNA molecules with a polynucleotide that encodes that polypeptide to form a duplex; and (b) detecting the duplex.

The present invention also provides preferred methods of detecting the polypeptide of the present invention comprising the steps of immunoreacting the polypeptide with an antibody to form an antibody-polypeptide conjugate, and detecting the conjugate, e.g., conjugating the antibodies to chemiluminescent molecules such as dioxytane-based molecules known in the art, for use as labelled probes. Thus, methods of detecting p235 protein in a sample are provided whereby antibody which specifically binds to p235 is administered to a sample, and binding is detected. It will be appreciated by those skilled in the art that such immunoassay methods include, without limitation, radioimmunoassays, enzyme-linked immunosorbent assays, "sandwich" assays, precipitin reactions, gel diffusion immunodiffusion assays, agglutination assays and immunoelectrophoresis assays.

In yet another embodiment, the present invention provides a polypeptide or fragment thereof having the amino acid sequence of SEQ ID NO: 2, capable of binding antibodies to p235. Preferably, the antibody is sequestered from a sample on a solid support. The polypeptide may comprise an indicator for conjugate detection, e.g., a chromophore, fluorophore, biotin moiety or an enzyme.

SPECIFIC EXAMPLE 3

Research Models

It will be appreciated that cell lines lacking expression of p235 may be prepared by methods known to those skilled in the art. For example, murine adipocytes and myocytes lacking expression of p235 may be generated by chemical mutagenesis (Pingel, et al., *Cell* 58:1055–1065 (1989) and Weaver et al., *Mol. Cell. Biol.* 11:4415–4422 (1991)) and/or gamma irradiation (Koretzky et al., *PNAS* (USA) 88:2037–2041 (1991)). Such cell lines may then be used to study the phosphoinositide cycle, including evaluating the role of p235, its substrates and products, as well as the effect of various compounds and compositions on the pathway. For example, whether a drug inhibits or activates (prevents or promotes) movement of glucose into cells, may be determined.

While the use of isolated cell lines is helpful in understanding the role of various proteins, more complete information can be obtained by studying the effects of these proteins directly in a mammal (i.e., an in vivo system). To this end, various mammals have been produced that have altered levels of expression of certain genes. One class of these mammals are the so called transgenic mammals. These mammals have a novel gene or genes, e.g., p235, introduced into their genome. Another class of these mammals is the so called knockout mammals, wherein expression of an endogenous gene, e.g., p235, has been suppressed through genetic manipulation.

Preparation of knockout mammal requires first introducing a nucleic acid construct that will be used to suppress expression of a particular gene into an undifferentiated cell type termed an embryonic stem cell. This cell is then injected into a mammalian embryo, where it hopefully will be integrated into the developing embryo. The embryo is then implanted into a foster mother for the duration of gestation.

Pfeffer et al. (*Cell*, 73:457–467 (1993)) describe mice in which the gene encoding the tumor necrosis factor receptor p55 has been suppressed. The mice showed a decreased response to tumor necrosis factor signaling.

Fung-Leung et al. (*Cell*, 65:443–449 (1991); *J. Exp. Med.*, 174:1425–1429 (1991)) describe knockout mice lacking expression of the gene encoding CD8. These mice were found to have a decreased level of cytotoxic T cell response to various antigens and to certain viral pathogens such as lymphocyte choriomeningitis virus.

U.S. Pat. No. 5,557,032 describes mice in which the gene encoding CD28 has been suppressed. Similarly, U.S. Pat. No. 5,714,667 describes mice in which expression of the gene encoding the CTLA-4 receptor is suppressed. Methods of making knockout mice are described in detail in U.S. Pat. No. 5,557,032.

The following describes in greater detail the materials and methods for producing the knockout mice of the present invention.

Preparation of knockout constructs. The DNA sequence to be used in producing the knockout construct (for example, and without limitation, the cDNA of SEQ ID NO: 1) is digested with a particular restriction enzyme selected to cut at a location(s) such that a new DNA sequence encoding a marker gene can be inserted in the proper position within this DNA sequence. The proper position for marker gene insertion is that which will serve to prevent expression of the native gene; this position will depend on various factors such as the restriction sites in the sequence to be cut, and whether an exon sequence or a promoter sequence, or both is (are) to be interrupted (i.e., the precise location of insertion necessary to inhibit promoter function or to inhibit synthesis of the native exon). Preferably, the enzyme selected for cutting the DNA will generate a longer arm and a shorter arm, where the shorter arm is at least about 300 base pairs (bp). In some cases, it will be desirable to actually remove a portion or even all of one or more exons of the gene to be suppressed so as to keep the length of the knockout construct comparable to the original genomic sequence when the marker gene is inserted in the knockout construct. In these cases, the genomic DNA is cut with appropriate restriction endonucleases such that a fragment of the proper size can be removed.

The marker gene can be any nucleic acid sequence that is detectable and/or assayable, however typically it is an antibiotic resistance gene or other gene whose expression or presence in the genome can be easily detected. The marker gene is usually operably linked to its own promoter or to another strong promoter from any source that will be active or can easily be activated in the cell into which it is inserted; however, the marker gene need not have its own promoter attached as it may be transcribed using the promoter of the gene to be suppressed. In addition, the marker gene will normally have a polyA sequence attached to the 3'end of the gene; this sequence serves to terminate transcription of the gene. Preferred marker genes are any antibiotic resistance gene such as neo (the neomycin resistance gene) and beta-gal (beta-galactosidase).

After the genomic DNA sequence has been digested with the appropriate restriction enzymes, the marker gene sequence is ligated into the genomic DNA sequence using methods well known to those skilled artisan and described in Sambrook et al., supra. The ends of the DNA fragments to be ligated must be compatible; this is achieved by either cuffing all fragments with enzymes that generate compatible ends, or by blunting the ends prior to ligation. Blunting is done using methods well known in the art, such as for example by the use of Kienow fragment (DNA polymerase I) to fill in sticky ends.

The ligated knockout construct may be inserted directly into embryonic stem cells (discussed below), or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

Transfection of embryonic stem cells. This invention contemplates production of knockout mammals from any species of rodent, including without limitation, rabbits, rats, hamsters, and mice. Preferred rodents include members of the Muridae family, including rats and mice. Generally, the embryonic stem cells (ES cells) used to produce the knockout mammal will be of the same species as the knockout mammal to be generated. Thus for example, mouse embryonic stem cells will usually be used for generation of knockout mice.

Embryonic stem cells are typically selected for their ability to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. A preferred ES cell line is murine cell line D3 (American Type Culture Collection catalog no. CRL 1934). The cells are cultured and prepared for DNA insertion using methods well known to the skilled artisan such as those set forth by Robertson, "Teratocarcinomas and Embryonic Stem Cells: A Practical Approach," E. J. Robertson, ed. IRL Press, Washington, D.C. (1987), Bradley et al. "Current Topics in Devel. Biol." 20:357–371 (1986) and Hogan et al. "Manipulating the Mouse Embryo: A Laboratory Manual," Cold Spring Harbor Laboratory Press, Cold Spring Harbor, N.Y. (1986).

Insertion of the knockout construct into the ES cells can be accomplished using a variety of methods well known in the art including for example, electroporation, microinjection, and calcium phosphate treatment (see Lovell-Badge, in Robertson, eds., supra). A preferred method of insertion is electroporation.

Each knockout construct DNA to be inserted into the cell must first be linearized if the knockout construct has been inserted into a vector. Linearization is accomplished by digesting the DNA with a suitable restriction endonuclease selected to cut only without the vector sequence and not within the knockout construct sequence.

For insertion of the DNA sequence, the knockout construct DNA is added to the ES cells under appropriate conditions for the insertion method chosen. Where more than one construct is to be introduced into the ES cell, DNA encoding each construct can be introduced simultaneously or one at a time.

If the cells are to be electroporated, the ES cells and knockout construct DNA are exposed to an electric pulse using an electroporation machine following the manufacturer's guidelines for use. After electroporation, the cells are allowed to recover under suitable incubation conditions. The cells are then screened for the presence of the knockout construct.

Screening can be done using a variety of methods. Where the marker gene is an antibiotic resistance gene, the cells are cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. Finally, if the marker gene is a gene the encodes an enzyme whose activity can be detected (e.g., beta-galactosidase), the enzyme substrate can be added to the cells under suitable conditions, and the enzymatic activity can be analyzed.

The knockout construct may be integrated into several locations in the ES cell genome, and may integrate into a different location in each cell's genome, due to the occurrence of random insertion events; the desired location of the insertion is in a complementary position to the DNA sequence to be knocked out. Typically, less than about 1–5 percent of the ES cells that take up the knockout construct will actually integrate the knockout construct in the desired location. To identify those cells with proper integration of the knockout construct, the DNA can be extracted from the cell using standard methods such as those described by Sambrook et al., supra. The DNA can then be probed on a Southern blot with a probe or probes designed to hybridize in a specific pattern to genomic DNA digested with a particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

Injection/implantation of embryos. After suitable ES cells containing the knockout construct in the proper location have been identified, the cells are inserted into an embryo. Insertion may be accomplished in a variety of ways, however, a preferred method is by microinjection. For microinjection, about 10–30 cells are collected into a micropipet and injected into embryos that are at the proper stage of development to integrate the ES cell into the developing embryo.

The suitable stage of development for the embryo is very species dependent, however, for mice it is about 3.5 days. The embryos are obtained by perfusing the uterus of pregnant females. Suitable methods for accomplishing this are known to the skilled artisan, and are set forth by Bradley (in Robertson, eds., supra).

While an embryo of the right age/stage of development is suitable for use, preferred embryos are male and have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo is implanted into the uterus of a pseudopregnant foster mother. While any foster mother may be used, they are typically selected for their ability to breed and reproduce well, and for their ability to care for their young. Such foster mothers are typically prepared by mating with vasectomized males of the same species. The stage of the pseudopregnant foster mother is important for successful implantation, and it is species dependent. For mice, this stage is about 2–3 days pseudopregnant.

Screening for presence of knockout gene. Offspring that are born to the foster mother may be screened initially for mosaic coat color where the coat color selection strategy (as described above) has been employed. In addition, or as an alternative, DNA from tail tissue of the offspring may be screened for the presence of the knockout constructing using Southern blot and/or PCR as described above. Offspring that appear to be mosaics are then crossed to each other if they are believed to carry the knockout construct in their germ line to generate homozygous knockout animals. If it is unclear whether the offspring will have germ line transmission, they can be crossed with a parental or other strain and the offspring screened for heterozygosity. The heterozygotes are identified by Southern blots and/or PCR amplification of the DNA, as set forth above.

The heterozygotes can then be crossed with each other to generate homozygous knockout offspring. Homozygotes may be identified by Southern blotting of equivalent amounts of genomic DNA from mice that are the product of this cross, as well as that are known heterozygotes and wild type mice. Probes to screen the Southern blots can be designed as set forth above.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the gene knocked out in various tissues of these offspring by probing the Western blot with an antibody against the protein encoded by the gene knocked out, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

It will be appreciated that the knockout mice provided herein may be used to screen for drugs useful in modulating the phosphoinositide cycle and in particular, the activity of p235, its substrates and products, i.e., drugs that may enhance or inhibit these activities. Screening for useful drugs would involve administering the candidate drug over a range of doses to the mouse, and assaying at various time points for the modulatory effect(s) of the drug on the system being evaluated. Such assays would include, for example, assaying for increased or decreased substrate and/or product levels, and/or increased or decreased levels of expression of particular genes involved in the cycle.

For example, a knockout mammal of the present invention could be used to screen a variety of compounds, either alone or in combination, to determine whether partial or total restoration or activation of the PIP5K activity results, e.g., whether glucose movement into a cell is promoted or prevented.

SPECIFIC EXAMPLE 4

Therapeutic Applications

The polynucleotides and proteins of the present invention are expected to exhibit one or more of the uses or biological activities (including those associated with assays cited herein) identified below. Use or activities described for proteins of the present invention may be provided by administration or use of such proteins or by administration or use of polynucleotides encoding such proteins (such as, for example, in gene therapies or vectors suitable for introduction of DNA).

A protein of the present invention (from whatever source derived, including without limitation from recombinant and non-recombinant sources) may thus be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s).

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example in, U.S. Pat. Nos. 4,235,871, 4,501,728, 4,837,028 and 4,737,323.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical compositions may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions be used to practice the method of the present invention should contain about 0.01 µg to about 100 mg (preferably about 0.1 µg to about 10 mg, more preferably about 0.1 µg to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the rage of 12 to 24 hours of continuous intravenous administration. Ultimately the attending physician will decide on the appropriate duration of intravenous therapy using the pharmaceutical composition of the present invention.

As set forth above, protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, *J. Amer. Chem. Soc.* 85:2149–2154 (1963) and J. L. Krstenansky, et al. *FEBS Lett.* 211:10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of diseases involving abnormal expression of the protein.

It will also be appreciated that the nucleotide sequences of the present invention may be used in gene therapy applications, e.g. to treat Type 2 diabetes. The methods of this invention thus comprise the step of introducing the nucleotide sequences of the present invention into a target cell. In order to effectuate transfer, the nucleotide sequences to be transferred must be associated with a vehicle capable of transducing the target cell. Those skilled in the art will appreciate that such vehicles include known gene therapy delivery systems including, but not limited to, adenoviral, retroviral and adeno-associated viral vectors, as well as liposomes and DNA-protein complexes.

The therapeutic compositions are also presently valuable for veterinary applications. Particularly, domestic animals and thoroughbred horses, in addition to humans, are desired patients for such treatment with proteins of the present invention.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

Patent and literature references cited herein are incorporated by reference as if fully set forth.

What is claimed is:

1. An isolated nucleic acid molecule encoding p235 comprising SEQ ID NO: 1.

2. A vector comprising the nucleic acid molecule of claim 1.

3. A cell transformed with the nucleic acid molecule of claim 1.

4. The cell of claim 3, wherein the cell is a mammalian cell.

5. The cell of claim 3, wherein the cell is a bacterial cell.

6. A transfected cell producing the protein encoded by the nucleic acid molecule of claim 1.

7. An isolated polynucleotide selected from the group consisting of:
   a) a polynucleotide comprising the nucleotide sequence of SEQ ID NO: 1,
   b) a polynucleotide encoding a protein comprising the amino acid sequence of SEQ ID NO: 2,
   c) a polynucleotide encoding a protein comprising a fragment of the amino acid sequence of SEQ ID NO: 2, having kinase activity, and,
   d) a polynucleotide which is an allelic variant of the polynucleotide of a).

8. An isolated polynucleotide of claim 6 wherein said polynucleotide is operably linked to an expression control sequence.

9. A host cell transformed with a polynucleotide of claim 8.

10. The host cell transformed with a polynucleotide of claim 9, wherein said cell is a mammalian cell.

11. The host cell of claim 9, wherein the cell is a bacterial cell.

12. A process for producing a protein encoded by a polynucleotide of claim 8, which process comprises:
    a) growing a culture of the host cell of claim 9 in a suitable culture medium; and
    b) purifying said protein from the culture.

13. A nucleic acid probe comprising at least a fragment of a nucleic acid molecule encoding a protein fragment having kinase activity comprising a nucleotide sequence capable of hybridizing under salt and temperature conditions of 6× SSC at about 45° C., followed by a wash of 0.2× SSC at 50° C. to the nucleotide sequence of SEQ ID NO: 1, wherein the probe is of a length sufficient to hybridize with a complementary nucleic acid sequence thereto.

14. A nucleic acid probe comprising at least a fragment of a nucleic acid molecule encoding a protein fragment having kinase activity comprising a nucleotide sequence capable of hybridizing under salt and temperature conditions of 6× SSC at about 45° C., followed by a wash of 0.2× SSC at 50° C. to the complement of the nucleotide sequence of SEQ ID NO: 1, wherein the probe is of a length sufficient to hybridize with a complementary nucleic acid sequence thereto.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 6297 base pairs
      (B) TYPE: nucleic acid
      (C) STRANDEDNESS: double
      (D) TOPOLOGY: linear (xi) SEQUENCE DESCRIPTION: SEQ ID NO:1:

```
GCTGGGCTTC TCGGCGCGAC CGCCGGCTGC CTGAGAAAGC CGGCCTGTGC TTGGCCTCGG      60

CTTCCCGGCC GAGAGTGGTG AGGCGGAGGC GGGAGGCGGG AGGCCCCGGG GGCGGGGCGG     120

GAGGCGAAGA CTCATGAAAT GGCCACAGAT GACAAGAGTT CCCCGACACT GGACTCTGCT     180

AATGATTTGC CTCGCTCTCC TGCCAGTCCT TCTCACCTCA CTCACTTTAA ACCCTTGACT     240

CCTGACCAGG ATGAGCCCCC CTTCAAGTCA GCATATAGTT CTTTTGTAAA CCTTTTTCGT     300

TTTAACAAAG AGCGAGGAGA AGGGGGCCAA GGAGAGCAGC AGTCTCCGAG TTCAAGTTGG     360

GCCAGCCCTC AGATCCCTTC AAGAACACAG TCTGTGAGGT CGCCTGTACC TTATAAAAAA     420

CAGCTTAATG AGGAGCTCCA CCGGCGCTCT TCAGTGTTAG AGAACACTTT GCCACATCCT     480

CAGGAGAGCA CAGACTCCAG AAGGAAAGCA GAACCAGCCT GTGGAGGTCA TGACCCACGT     540

ACAGCTGTTC AGCTTCGAAG CCTCAGCACA GTATTGAAAC GCCTCAAAGA AATCATGGAA     600

GGAAAAAGCC AGGACAGTGA CCTGAAGCAA TATTGGATGC CAGATAGCCA GTGTAAAGAG     660

TGCTATGACT GCAGTGAAAA GTTTACAACA TTTAGGCGCA GACACCATTG CAGACTGTGT     720

GGGCAGATTT TCTGCAGTCG TTGTTGTAAT CAAGAAATCC CTGGAAAATT TATGGGCTAT     780

ACAGGAGACC TCCGAGCATG CACCTACTGT AGAAAAATAG CCTTAAGTTA TGCTCATTCT     840

ACAGACAGTA ATTCCATTGG GGAAGACTTG AATGCTCTTT CAGATTCAAC TTGCTCTGTG     900

TCTATACTTG ATCCAAGCGA ACCTCGGACA CCAGTTGGGA GTAGAAAAGC CAGTCGTAAC     960

ATATTCTTAG AGGATGATTT AGCCTGGCAA AGCTTGATTC ATCCGGATTC CTCAAATAGT    1020

GCTCTTTCAA CAAGACTCGT ATCTGTTCAA GAGGATGCTG GGAAGTCTCC TGCTCGAAAC    1080

AGATCAGCCA GCATTACTAA TCTGTCACTG GATCGGTCTG GTTCTCCTAT GGTTCCTTCA    1140

TATGAGACAT CTGTCAGTCC CCAGGCTAAC CGAAACTACA TTAGGACAGA GACGACTGAG    1200
```

-continued

```
GATGAACGCA AAATTCTTCT GGACAGTGCT CAGTTAAAGG ATCTGTGGAA GAAAATCTGC   1260

CATCACACCA GTGGGATGGA ATTTCAAGAT CACCGTTACT GGTTGAGAAC ACATCCCAAC   1320

TGCATTGTAG GGAAGGAATT AGTCAACTGG CTAATCAGAA ATGGACACAT CGCTACAAGG   1380

GCACAAGCTA TAGCAATTGG ACAAGCAATG GTTGATGGAC GTTGGTTGGA TTGTGTTAGT   1440

CATCATGATC AGCTTTTCAG GGACGAATAT GCGTTGTATA GACCACTTCA GAGTACAGAA   1500

TTTTCTGAGA CACCTTCTCC AGACAGTGAC TCTGTGAACT CTGTGGAAGG ACACTCCGAG   1560

CCATCCTGGT TTAAAGACAT AAAATTTGAT GACAGTGACA CAGAACAGAT TGCTGAAGAA   1620

GGTGACGATA ATTTGGCTAA GTATTTGGTT TCTGACACTG GAGGACAGCA GCTCTCAATA   1680

AGTGATGCCT TCATCAAAGA GTCCTTATTT AATCGACGAG TAGAGGAAAA ATCCAAAGAG   1740

CTGCCTTTTA CCCCTTTGGG CTGGCATCAT AACAACCTGG AACTCTTGCG AGAGGAGAAT   1800

GAGGAGAAGC AAGCCATGGA AAGGCTGCTT TCAGCTAATC ATAACCACAT GATGGCCCTA   1860

CTCCAGCAGT TGCTTCAAAA CGAGTCATTG TCATCGTCTT GGAGGGACAT CATTGTGTCA   1920

CTAGTCTGCC AGGTTGTTCA GACAGTCCGA CCTGATGTCA AGCACCAGGA TGATGACATG   1980

GATATCCGTC AGTTTGTCCA TATCAAGAAG ATCCCAGGTG GAAAGAAATT TGACTCTGTG   2040

GTTGTCAATG GCTTTGTTTG TACCAAGAAC ATTGCACATA AAAAGATGAA TTCCTGTATT   2100

AAAAACCCCA AAATCCTTCT GTTGAAGTGT TCTATTGAGT ATCTCTATAG AGAAGAAACT   2160

AAGTTTACCT GCATTGATCC TATTGTGCTT CAGGAAAGGG AATTCTTGAA GAATTATGTT   2220

CAACGAATAG TTGATGTTCG ACCCACATTG GTTCTTGTTG AGAAAACAGT GTCTCGGATT   2280

GCTCAGGACA TGTTACTGGA ACATGGCATT ACTCTGGTCA TTAATGTAAA GTCACAAGTT   2340

TTAGAAAGAA TCAGTCGAAT GACCCAAGGT GATTTAGTGG TGTCCATGGA CCAGCTGCTC   2400

ACCAAACCCC ACTTGGGCAC TTGCCACAAA TTTTATATGC AGATATTTCA GCTGCCTAAT   2460

GAACAAACCA AAACACTGAT GTTTTTTGAA GGTTGTCCAC AGCATCTAGG CTGCACAATC   2520

AAGCTCAGAG GAGGCTCTGA TTATGAGCTG GCTCGAGTTA AGGAGATCCT AATATTTATG   2580

ATCTGTGTAG CTTATCATTC TCAGCTAGAA ATCTCTTTTC TCATGGATGA GTTCGCTATG   2640

CCTCCAACAT TAATGCAAAG CCCTTCATTC CATCTTCTGA CGGAGGGACG AGGTGAAGAG   2700

GGAGCCTCTC AGGAGCAGGT CAGTGGCAGC TCCCTTCCTC AGGATCCTGA GTGCCCTCGT   2760

GAGGCCCTGT CTTCTGAGGA TAGCACTTTG TTGGAATCAA GGACTGTGCT AGAGAAGGGT   2820

GAACTAGACA ATAAAAGTAT TCCACAAGCT GTTGCCTCTT TGAAGCATCA AGATTATACC   2880

ACCCCCACTT GCCCAGCAGG TATTCCCTGT GCTCTTTTTG CATTGGTACC AGAGTCATTG   2940

TTGCCTCTCC ATATGGATCA ACAGGATGCC GTAGGAAATG AACACCGAGA GACTTCACAG   3000

CAAACGGATG AGCAACAGGA TCCCAAAAGC CAGATGAAAG CTTTTAGAGA CCCTTTACAG   3060

GATGACACTG GAATGTACGT TACTGAGGAA GTCACCTCCT CTGAAGATCA ACGAAAGACT   3120

TATGCCTTGA CATTTAAACA GGAGTTAAAA GATGTAATCC TCTGTATCTC TCCAGTTATT   3180

ACATTCCGTG AACCTTTCCT TTTAACTGAA AAGGGGATGA GATGCTCAAC TCGAGATTAT   3240

TTTCCAGAGC AGATTTACTG GTCTCCTCTT CTCAACAAAG AGGTGAAGGA AATGGAGAGC   3300

AGGAGGAAGA AACAGCTGCT CAGGGATCTC TCTGGACTTC AGGGCATGAA TGGCAGTGTT   3360

CAGGCCAAGT CTATTCAAGT CTTACCCTCA CATGAGCTAG TGAGCACCAG GATTGCTGAA   3420

CATGTGGGTG ACAGCCAGAC CTTGGGTAGA ATGCTAGCTG ATTATCGAGC TAGAGGAGGA   3480

GAATTCAGTC AAAACATTTG GAACCCCTTT GTCCATTCAA AAGATGACAT CATGTACTTC   3540

AGGTGGCAAA TCAGGGAAAC AAAACTGAGA GTGATGAAAG AGAGGGGATT GATTCCAAGT   3600
```

-continued

```
GATGTAATAT GGCCAACAAA GGTGGACTGT CTGAACCCTG CTAACCACCA GAGGCTCTGT    3660

GTGCTCTTCA GCAGCTCTTC TGCCCAGTCC AGCAATGCTC CCAGTGCTTG TGTCAGTCCT    3720

TGGATTGTAA CAATGGAGTT TTATGGAAAG AATGACCTTA CACTGGGGAT ATTTTTAGAA    3780

AGATACTGTT TCAGGTACTC TTACCAGTGT CCGAGCATGT TCTGTGACAC CCCCATGGTT    3840

CATCACATTC GACGCTTTGT TCATGGCCAA GGCTGTGTAC AGATAATTCT GAAGGAGTTG    3900

GATTCTCCAG TGCCTGGATA TCAACATACA ATTCTCACAT ATTCCTGGTG CAGAATCTGC    3960

AAACAAGTAA CACCAGTTGT TGCTCTTTCA AATGAATCCT GGTCTATGTC ATTTGCAAAG    4020

TACCTTGAAC TTCGATTTTA TGGCCACCAG TACACACGCA GAGCCAACGC TGAGCCCTGC    4080

GGTCACTCTA TCCACCATGA TTATCACCAG TATTTCTCTT ATAACCAGAT GGTGGCATCT    4140

TTCAGTTACT CTCCTATTCG GCTTCTTGAA GTATGTGTTC CACTACCAAA AATATTCATT    4200

AAGCGTCAAG CCCCACTGAA GGTATCTCTT CTTCAGGACC TCAAAGACTT TTTTCAGAAG    4260

GTTTCACAGG TGTACCTAGC TGTTGATGAG AGACTTGCAT CCTTGAAAAC GGATACATTT    4320

AGCAAAACTA GAGAGGAAAA GATGGAAGAT ATCTTTGCAC AAAAGGAGAT GGAAGAGGGT    4380

GAGTTTAAGA ACTGGACAGA GAAGATGCAA GCAAGGCTCA TGTCTTCCTC TGTGGATACC    4440

CCTCAGCAAC TGCAGTCCAT TTTTGAGTCA CTGATTGCCA AGAAGCAAAG CCTCTGTGAG    4500

GTGCTCCAGG CGTGGAACAG CAGGTTGCAG GACCTCTTCC AGCAGGAAAA AGGTAGAAAG    4560

AGGCCTTCAG TTCCTCCCAG TCCTGGGAGA CTGAGACAAG GTGAAGAAAG CAAGATAAAT    4620

GCAATGGACA CATCTCCAAG GAATATTTCT CCAGGACTTT CACAATGGAG AAAAAGAAGA    4680

TCGCTTCTTG ACAACCCTGT CCAGCCAGCT ACGAGCTCCA CCCACCTCCA GCTGCCCACT    4740

CCTCCCGAGG CCCTGGCCGA GCAGGTAGTG GGAGGGCCGA CTGATCTGGA TTCAGCCAGT    4800

GGCTCTGAAG ATGTATTTGA TGGTCATTTG CTGGGATCCA CAGACAGCCA GGTGAAGGAA    4860

AAGTCAACCA TGAAAGCCAT CTTTGCTAAT TTGCTTCCAG GAAACAGCTA CAATCCCATT    4920

CCATTTCCTT TTGATCCAGA TAAACACTAC TTAATGTATG AACATGAACG GGTGCCCATT    4980

GCTGTCTGTG AGAAAGAGCC CAGCTCCATC ATTGCTTTTG CACTCAGTTG TAAAGAATAC    5040

CGCAATGCCT TAGAGGAATT GTCCAAAGCA ACTCTGCGGA ACAGTGCTGA AGAAGGGCTC    5100

CCAGCCAATA GTGCTTTAGA TAACAGACCT AAGAGTAGCA GCCCTATTAG ACTACCTGAA    5160

ATCAGTGGAG ACAGACAAA CCGCACAGTA GAAGCAGAAC CTCAGCCAAC CAAAAAAGCT    5220

TCAGGAATGT TGTCCTTCTT CAGAGGAACA GCAGGGAAGA GCCCTGATCT GTCTTCCCAG    5280

AAGAGGGAGA CCTTGCGAGG GGCAGACAGT GCTTACTACC AGGTTGGGCA GGCCGGCAAG    5340

GAGGGGTTGG AGAGTCAAGG CCTGGAGCCT CAAGATGAAG TAGATGGAGG AGATACACAG    5400

AAGAAACAAC TCACAAATCC TCATGTGGAA CTTCAATTTT CTGATGCTAA TGCCAAGTTT    5460

TACTGTCGGC TGTACTACGC GGGAGAGTTC CACAAGATGC GTGAAGTGAT TCTGGGCAGC    5520

AGTGAGGAGG AATTCATCCG TTCCCTTTCT CACTCATCTC CCTGGCAGGC CCGGGGAGGC    5580

AAGTCAGGAG CTGCTTTCTA TGCCACCGAA GATGATAGAT TCATTCTGAA GCAAATGCCT    5640

CGTTTGGAAG TCCAGTCTTT CCTTGACTTT GCACCACACT ACTTCAATTA TATCACAAAT    5700

GCTGTTCAAC AAAAGAGGCC CACCGCCTTG GCTAAAATTC TTGGAGTTTA CAGAATTGGT    5760

TATAAGAACT CTCAGAACAA CACTGAGAAG AAGTTAGATC TCCTTGTCAT GGAAAATCTT    5820

TTCTATGGGA GAAAGATGGC ACAGGTTTTT GATTTGAAGG GTTCACTTAG GAATCGAAAT    5880

GTAAAAACTG ACACTGGGAA AGAGAGCTGT GATGTGGTTC TGTTGGATGA AAACCTCCTA    5940

AAGATGGTTC GAGACAACCC TCTCTATATT CGTTCCCATT CCAAATCTGA GCTGAGAACC    6000
```

-continued

```
TCCATCCACA GCGACGCCCA TTTCCTTTCC AGCCACCTCA TTATAGACTA TTCTCTGCTG    6060

GTTGGGCGAG ATGACACTAG CAATGAGCTT GTGGTTGGCA TCATAGATTA CATTCGAACA    6120

TTTACATGGG ACAAAAAACT TGAGATGGTT GTGAAGTCAA CAGGAATTTT AGGAGGACAA    6180

GGTAAAATGC CAACTGTGGT CTCTCCAGAG TTGTATAGGA CTAGATTTTG TGAAGCAATG    6240

GACAAGTATT TCTTGATGGT GCCAGACCAC TGGACAGGGT TGGATCTGAA TTGCTGA      6297
```

(2) INFORMATION FOR SEQ ID NO:2:

(i) SEQUENCE CHARACTERISTICS:
        (A) LENGTH: 2052 amino acids
        (B) TYPE: amino acid
        (C) STRANDEDNESS: unknown
        (D) TOPOLOGY: unknown (xi) SEQUENCE DESCRIPTION: SEQ ID NO:2:

```
Met Ala Thr Asp Asp Lys Ser Ser Pro Thr Leu Asp Ser Ala Asn Asp
1               5                   10                  15

Leu Pro Arg Ser Pro Ala Ser Pro Ser His Leu Thr His Phe Lys Pro
            20                  25                  30

Leu Thr Pro Asp Gln Asp Glu Pro Phe Lys Ser Ala Tyr Ser Ser
        35                  40                  45

Phe Val Asn Leu Phe Arg Phe Asn Lys Glu Arg Gly Glu Gly Gly Gln
    50                  55                  60

Gly Glu Gln Gln Ser Pro Ser Ser Trp Ala Ser Pro Gln Ile Pro
65                  70                  75                  80

Ser Arg Thr Gln Ser Val Arg Ser Pro Val Pro Tyr Lys Lys Gln Leu
                85                  90                  95

Asn Glu Glu Leu His Arg Arg Ser Ser Val Leu Glu Asn Thr Leu Pro
            100                 105                 110

His Pro Gln Glu Ser Thr Asp Ser Arg Arg Lys Ala Glu Pro Ala Cys
        115                 120                 125

Gly Gly His Asp Pro Arg Thr Ala Val Gln Leu Arg Ser Leu Ser Thr
    130                 135                 140

Val Leu Lys Arg Leu Lys Glu Ile Met Glu Gly Lys Ser Gln Asp Ser
145                 150                 155                 160

Asp Leu Lys Gln Tyr Trp Met Pro Asp Ser Gln Cys Lys Glu Cys Tyr
                165                 170                 175

Asp Cys Ser Glu Lys Phe Thr Thr Phe Arg Arg Arg His His Cys Arg
            180                 185                 190

Leu Cys Gly Gln Ile Phe Cys Ser Arg Cys Cys Asn Gln Glu Ile Pro
        195                 200                 205

Gly Lys Phe Met Gly Tyr Thr Gly Asp Leu Arg Ala Cys Thr Tyr Cys
    210                 215                 220

Arg Lys Ile Ala Leu Ser Tyr Ala His Ser Thr Asp Ser Asn Ser Ile
225                 230                 235                 240

Gly Glu Asp Leu Asn Ala Leu Ser Asp Ser Thr Cys Ser Val Ser Ile
                245                 250                 255

Leu Asp Pro Ser Glu Pro Arg Thr Pro Val Gly Ser Arg Lys Ala Ser
            260                 265                 270

Arg Asn Ile Phe Leu Glu Asp Asp Leu Ala Trp Gln Ser Leu Ile His
        275                 280                 285

Pro Asp Ser Ser Asn Ser Ala Leu Ser Thr Arg Leu Val Ser Val Gln
    290                 295                 300
```

-continued

```
Glu Asp Ala Gly Lys Ser Pro Ala Arg Asn Arg Ser Ala Ser Ile Thr
305                 310                 315                 320

Asn Leu Ser Leu Asp Arg Ser Gly Ser Pro Met Val Pro Ser Tyr Glu
            325                 330                 335

Thr Ser Val Ser Pro Gln Ala Asn Arg Asn Tyr Ile Arg Thr Glu Thr
            340                 345                 350

Thr Glu Asp Glu Arg Lys Ile Leu Leu Asp Ser Ala Gln Leu Lys Asp
            355                 360                 365

Leu Trp Lys Lys Ile Cys His His Thr Ser Gly Met Glu Phe Gln Asp
    370                 375                 380

His Arg Tyr Trp Leu Arg Thr His Pro Asn Cys Ile Val Gly Lys Glu
385                 390                 395                 400

Leu Val Asn Trp Leu Ile Arg Asn Gly His Ile Ala Thr Arg Ala Gln
                405                 410                 415

Ala Ile Ala Ile Gly Gln Ala Met Val Asp Gly Arg Trp Leu Asp Cys
            420                 425                 430

Val Ser His His Asp Gln Leu Phe Arg Asp Glu Tyr Ala Leu Tyr Arg
            435                 440                 445

Pro Leu Gln Ser Thr Glu Phe Ser Glu Thr Pro Ser Pro Asp Ser Asp
    450                 455                 460

Ser Val Asn Ser Val Glu Gly His Ser Glu Pro Ser Trp Phe Lys Asp
465                 470                 475                 480

Ile Lys Phe Asp Asp Ser Asp Thr Glu Gln Ile Ala Glu Glu Gly Asp
            485                 490                 495

Asp Asn Leu Ala Lys Tyr Leu Val Ser Asp Thr Gly Gly Gln Gln Leu
            500                 505                 510

Ser Ile Ser Asp Ala Phe Ile Lys Glu Ser Leu Phe Asn Arg Arg Val
    515                 520                 525

Glu Glu Lys Ser Lys Glu Leu Pro Phe Thr Pro Leu Gly Trp His His
530                 535                 540

Asn Asn Leu Glu Leu Leu Arg Glu Gly Asn Glu Glu Lys Gln Ala Met
545                 550                 555                 560

Glu Arg Leu Leu Ser Ala Asn His Asn His Met Met Ala Leu Leu Gln
                565                 570                 575

Gln Leu Leu Gln Asn Glu Ser Leu Ser Ser Ser Trp Arg Asp Ile Ile
            580                 585                 590

Val Ser Leu Val Cys Gln Val Val Gln Thr Val Arg Pro Asp Val Lys
            595                 600                 605

His Gln Asp Asp Asp Met Asp Ile Arg Gln Phe Val His Ile Lys Lys
    610                 615                 620

Ile Pro Gly Gly Lys Lys Phe Asp Ser Val Val Asn Gly Phe Val
625                 630                 635                 640

Cys Thr Lys Asn Ile Ala His Lys Lys Met Asn Ser Cys Ile Lys Asn
            645                 650                 655

Pro Lys Ile Leu Leu Leu Lys Cys Ser Ile Glu Tyr Leu Tyr Arg Glu
            660                 665                 670

Glu Thr Lys Phe Thr Cys Ile Asp Pro Ile Val Leu Gln Glu Arg Glu
            675                 680                 685

Phe Leu Lys Asn Tyr Val Gln Arg Ile Val Asp Val Arg Pro Thr Leu
    690                 695                 700

Val Leu Val Glu Lys Thr Val Ser Arg Ile Ala Gln Asp Met Leu Leu
705                 710                 715                 720
```

-continued

```
Glu His Gly Ile Thr Leu Val Ile Asn Val Lys Ser Gln Val Leu Glu
            725                 730                 735

Arg Ile Ser Arg Met Thr Gln Gly Asp Leu Val Val Ser Met Asp Gln
            740                 745                 750

Leu Leu Thr Lys Pro His Leu Gly Thr Cys His Lys Phe Tyr Met Gln
            755                 760                 765

Ile Phe Gln Leu Pro Asn Glu Gln Thr Lys Thr Leu Met Phe Phe Glu
            770                 775                 780

Gly Cys Pro Gln His Leu Gly Cys Thr Ile Lys Leu Arg Gly Gly Ser
785                 790                 795                 800

Asp Tyr Glu Leu Ala Arg Val Lys Glu Ile Leu Ile Phe Met Ile Cys
            805                 810                 815

Val Ala Tyr His Ser Gln Leu Glu Ile Ser Phe Leu Met Asp Glu Phe
            820                 825                 830

Ala Met Pro Pro Thr Leu Met Gln Ser Pro Ser Phe His Leu Leu Thr
            835                 840                 845

Glu Gly Arg Gly Glu Glu Gly Ala Ser Gln Glu Gln Val Ser Gly Ser
            850                 855                 860

Ser Leu Pro Gln Asp Pro Glu Cys Pro Arg Glu Ala Leu Ser Ser Glu
865                 870                 875                 880

Asp Ser Thr Leu Leu Glu Ser Arg Thr Val Leu Glu Lys Gly Glu Leu
            885                 890                 895

Asp Asn Lys Ser Ile Pro Gln Ala Val Ala Ser Leu His Gln Asp
            900                 905                 910

Tyr Thr Thr Pro Thr Cys Pro Ala Gly Ile Pro Cys Ala Leu Phe Ala
            915                 920                 925

Leu Val Pro Glu Ser Leu Leu Pro Leu His Met Asp Gln Gln Asp Ala
            930                 935                 940

Val Gly Asn Glu His Arg Glu Thr Ser Gln Gln Thr Asp Glu Gln Gln
945                 950                 955                 960

Asp Pro Lys Ser Gln Met Lys Ala Phe Arg Asp Pro Leu Gln Asp Asp
            965                 970                 975

Thr Gly Met Tyr Val Thr Glu Glu Val Thr Ser Ser Glu Asp Gln Arg
            980                 985                 990

Lys Thr Tyr Ala Leu Thr Phe Lys Gln Glu Leu Lys Asp Val Ile Leu
            995                 1000                1005

Cys Ile Ser Pro Val Ile Thr Phe Arg Glu Pro Phe Leu Leu Thr Glu
            1010                1015                1020

Lys Gly Met Arg Cys Ser Thr Arg Asp Tyr Phe Pro Glu Gln Ile Tyr
1025                1030                1035                1040

Trp Ser Pro Leu Leu Asn Lys Glu Val Lys Glu Met Glu Ser Arg Arg
            1045                1050                1055

Lys Lys Gln Leu Leu Arg Asp Leu Ser Gly Leu Gln Gly Met Asn Gly
            1060                1065                1070

Ser Val Gln Ala Lys Ser Ile Gln Val Leu Pro Ser His Glu Leu Val
            1075                1080                1085

Ser Thr Arg Ile Ala Glu His Val Gly Asp Ser Gln Thr Leu Gly Arg
            1090                1095                1100

Met Leu Ala Asp Tyr Arg Ala Arg Gly Gly Glu Phe Ser Gln Asn Ile
1105                1110                1115                1120

Trp Asn Pro Phe Val His Ser Lys Asp Asp Ile Met Tyr Phe Arg Trp
            1125                1130                1135
```

-continued

```
Gln Ile Arg Glu Thr Lys Leu Arg Val Met Lys Glu Arg Gly Leu Ile
        1140                1145                1150
Pro Ser Asp Val Ile Trp Pro Thr Lys Val Asp Cys Leu Asn Pro Ala
        1155                1160                1165
Asn His Gln Arg Leu Cys Val Leu Phe Ser Ser Ser Ala Gln Ser
        1170                1175                1180
Ser Asn Ala Pro Ser Ala Cys Val Ser Pro Trp Ile Val Thr Met Glu
1185                1190                1195                1200
Phe Tyr Gly Lys Asn Asp Leu Thr Leu Gly Ile Phe Leu Glu Arg Tyr
                1205                1210                1215
Cys Phe Arg Tyr Ser Tyr Gln Cys Pro Ser Met Phe Cys Asp Thr Pro
                1220                1225                1230
Met Val His His Ile Arg Arg Phe Val His Gly Gln Gly Cys Val Gln
        1235                1240                1245
Ile Ile Leu Lys Glu Leu Asp Ser Pro Val Pro Gly Tyr Gln His Thr
        1250                1255                1260
Ile Leu Thr Tyr Ser Trp Cys Arg Ile Cys Lys Gln Val Thr Pro Val
1265                1270                1275                1280
Val Ala Leu Ser Asn Glu Ser Trp Ser Met Ser Phe Ala Lys Tyr Leu
                1285                1290                1295
Glu Leu Arg Phe Tyr Gly His Gln Tyr Thr Arg Arg Ala Asn Ala Glu
                1300                1305                1310
Pro Cys Gly His Ser Ile His His Asp Tyr His Gln Tyr Phe Ser Tyr
                1315                1320                1325
Asn Gln Met Val Ala Ser Phe Ser Tyr Ser Pro Ile Arg Leu Leu Glu
        1330                1335                1340
Val Cys Val Pro Leu Pro Lys Ile Phe Ile Lys Arg Gln Ala Pro Leu
1345                1350                1355                1360
Lys Val Ser Leu Leu Gln Asp Leu Lys Asp Phe Phe Gln Lys Val Ser
                1365                1370                1375
Gln Val Tyr Leu Ala Val Asp Glu Arg Leu Ala Ser Leu Lys Thr Asp
                1380                1385                1390
Thr Phe Ser Lys Thr Arg Glu Glu Lys Met Glu Asp Ile Phe Ala Gln
                1395                1400                1405
Lys Glu Met Glu Glu Gly Glu Phe Lys Asn Trp Thr Glu Lys Met Gln
        1410                1415                1420
Ala Arg Leu Met Ser Ser Ser Val Asp Thr Pro Gln Gln Leu Gln Ser
1425                1430                1435                1440
Ile Phe Glu Ser Leu Ile Ala Lys Lys Gln Ser Leu Cys Glu Val Leu
                1445                1450                1455
Gln Ala Trp Asn Ser Arg Leu Gln Asp Leu Phe Gln Gln Glu Lys Gly
                1460                1465                1470
Arg Lys Arg Pro Ser Val Pro Pro Ser Pro Gly Arg Leu Arg Gln Gly
                1475                1480                1485
Glu Glu Ser Lys Ile Asn Ala Met Asp Thr Ser Pro Arg Asn Ile Ser
        1490                1495                1500
Pro Gly Leu Ser Gln Trp Arg Lys Arg Arg Ser Leu Leu Asp Asn Pro
1505                1510                1515                1520
Val Gln Pro Ala Thr Ser Ser Thr His Leu Gln Leu Pro Thr Pro Pro
                1525                1530                1535
Glu Ala Leu Ala Glu Gln Val Val Gly Gly Pro Thr Asp Leu Asp Ser
                1540                1545                1550
```

-continued

```
Ala Ser Gly Ser Glu Asp Val Phe Asp Gly His Leu Leu Gly Ser Thr
        1555            1560                1565

Asp Ser Gln Val Lys Glu Lys Ser Thr Met Lys Ala Ile Phe Ala Asn
        1570            1575                1580

Leu Leu Pro Gly Asn Ser Tyr Asn Pro Ile Pro Phe Pro Phe Asp Pro
1585            1590                1595                1600

Asp Lys His Tyr Leu Met Tyr Glu His Glu Arg Val Pro Ile Ala Val
        1605            1610                1615

Cys Glu Lys Glu Pro Ser Ser Ile Ile Ala Phe Ala Leu Ser Cys Lys
        1620            1625                1630

Glu Tyr Arg Asn Ala Leu Glu Glu Leu Ser Lys Ala Thr Leu Arg Asn
        1635            1640                1645

Ser Ala Glu Glu Gly Leu Pro Ala Asn Ser Ala Leu Asp Asn Arg Pro
        1650            1655                1660

Lys Ser Ser Ser Pro Ile Arg Leu Pro Glu Ile Ser Gly Gly Gln Thr
1665            1670                1675                1680

Asn Arg Thr Val Glu Ala Glu Pro Gln Pro Thr Lys Lys Ala Ser Gly
        1685            1690                1695

Met Leu Ser Phe Phe Arg Gly Thr Ala Gly Lys Ser Pro Asp Leu Ser
        1700            1705                1710

Ser Gln Lys Arg Glu Thr Leu Arg Gly Ala Asp Ser Ala Tyr Tyr Gln
        1715            1720                1725

Val Gly Gln Ala Gly Lys Glu Gly Leu Glu Ser Gln Gly Leu Glu Pro
        1730            1735                1740

Gln Asp Glu Val Asp Gly Gly Asp Thr Gln Lys Lys Gln Leu Thr Asn
1745            1750                1755                1760

Pro His Val Glu Leu Gln Phe Ser Asp Ala Asn Ala Lys Phe Tyr Cys
        1765            1770                1775

Arg Leu Tyr Tyr Ala Gly Glu Phe His Lys Met Arg Glu Val Ile Leu
        1780            1785                1790

Gly Ser Ser Glu Glu Glu Phe Ile Arg Ser Leu Ser His Ser Ser Pro
        1795            1800                1805

Trp Gln Ala Arg Gly Gly Lys Ser Gly Ala Ala Phe Tyr Ala Thr Glu
        1810            1815                1820

Asp Asp Arg Phe Ile Leu Lys Gln Met Pro Arg Leu Glu Val Gln Ser
1825            1830                1835                1840

Phe Leu Asp Phe Ala Pro His Tyr Phe Asn Tyr Ile Thr Asn Ala Val
        1845            1850                1855

Gln Gln Lys Arg Pro Thr Ala Leu Ala Lys Ile Leu Gly Val Tyr Arg
        1860            1865                1870

Ile Gly Tyr Lys Asn Ser Gln Asn Asn Thr Glu Lys Lys Leu Asp Leu
        1875            1880                1885

Leu Val Met Glu Asn Leu Phe Tyr Gly Arg Lys Met Ala Gln Val Phe
        1890            1895                1900

Asp Leu Lys Gly Ser Leu Arg Asn Arg Asn Val Lys Thr Asp Thr Gly
1905            1910                1915                1920

Lys Glu Ser Cys Asp Val Val Leu Leu Asp Glu Asn Leu Leu Lys Met
        1925            1930                1935

Val Arg Asp Asn Pro Leu Tyr Ile Arg Ser His Ser Lys Ser Glu Leu
        1940            1945                1950

Arg Thr Ser Ile His Ser Asp Ala His Phe Leu Ser Ser His Leu Ile
        1955            1960                1965
```

-continued

```
Ile Asp Tyr Ser Leu Leu Val Gly Arg Asp Asp Thr Ser Asn Glu Leu
    1970                1975                1980

Val Val Gly Ile Ile Asp Tyr Ile Arg Thr Phe Thr Trp Asp Lys Lys
1985                1990                1995                2000

Leu Glu Met Val Val Lys Ser Thr Gly Ile Leu Gly Gly Gln Gly Lys
                    2005                2010                2015

Met Pro Thr Val Val Ser Pro Glu Leu Tyr Arg Thr Arg Phe Cys Glu
                2020                2025                2030

Ala Met Asp Lys Tyr Phe Leu Met Val Pro Asp His Trp Thr Gly Leu
            2035                2040            2045

Asp Leu Asn Cys
    2050
```